United States Patent [19]

Picard et al.

[11] Patent Number: 5,420,339

[45] Date of Patent: May 30, 1995

[54] ALPHA-ARYL OR HETEROARYL-SUBSTITUTED AMIDE ESTER ACAT INHIBITORS

[75] Inventors: Joseph A. Picard; Drago R. Sliskovic, both of Ypsilanti, Mich.

[73] Assignee: Warner-Lambert Company, Morris Plains, N.J.

[21] Appl. No.: 156,225

[22] Filed: Nov. 22, 1993

[51] Int. Cl.$^6$ .................... C07C 229/36; A61K 31/24
[52] U.S. Cl. ...................... 560/43; 544/329; 544/332; 560/37; 560/44
[58] Field of Search .............. 560/43, 37, 44; 514/539, 256, 275, 530, 531, 533; 544/329, 332

[56] References Cited

U.S. PATENT DOCUMENTS

| | | | |
|---|---|---|---|
| 5,079,137 | 1/1992 | Taguchi et al. | 430/559 |
| 5,123,951 | 6/1992 | See et al. | 71/86 |
| 5,334,747 | 8/1994 | Steffen et al. | 560/43 |

FOREIGN PATENT DOCUMENTS 9115464 10/1991 WIPO .

*Primary Examiner*—José G. Dees
*Assistant Examiner*—Barbara S. Frazier
*Attorney, Agent, or Firm*—Michael J. Atkins; Charles W. Ashbrook

[57] ABSTRACT

Pharmaceutically useful compounds having acylcoenzyme A: cholesterol acyltransferase inhibitory activity having the general formula

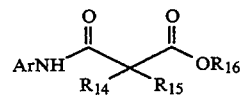

wherein Ar is di- or trisubstituted aryl or heteroaryl; $R_{14}$ and $R_{15}$ are each independently aryl, heteroaryl, hydrogen, fluorine, or alkyl, with the proviso that $R_{14}$ and $R_{15}$ are not both hydrogen, fluorine, or a straight or branched chain alkyl or a combination thereof; and $R_{16}$ is a straight or branched hydrocarbon chain having 1 to 20 carbon atoms and is saturated or unsaturated and has 1 to 3 double bonds, the double bonds being adjacent or nonadjacent.

13 Claims, No Drawings

ALPHA-ARYL OR HETEROARYL-SUBSTITUTED AMIDE ESTER ACAT INHIBITORS

BACKGROUND OF THE INVENTION

This invention relates to chemical compounds having pharmacological activity, to pharmaceutical compositions which include these compounds, and to a pharmaceutical method of treatment. More particularly, this invention concerns certain malonamide esters, compounds which inhibit the enzyme acylcoenzyme A:-cholesterol acyltransferase (ACAT), pharmaceutical compositions containing these compounds, and a method of treating hypercholesterolemia and atherosclerosis.

In recent years the role which elevated blood plasma levels of cholesterol play in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting primarily of phospholipids and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

U.S. Ser. No. 508,315, filed Apr. 11, 1990, now abandoned, and U.S. Ser. No. 667,813 filed Mar. 15, 1991, now abandoned, and related Patent Cooperation Treaty Application PCT/US91/02441 filed Apr. 9, 1991, and published as WO91/15464 on Oct. 17, 1991, disclose amide ester ACAT inhibitors of the following formula:

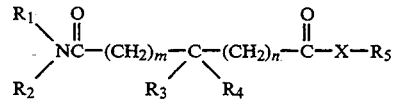

wherein each of m and n is independently 0, 1, or 2,
wherein X is oxygen or sulfur;
wherein each of $R_1$ and $R_2$ is independently
(a) hydrogen,
(b) the group

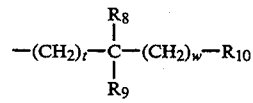

wherein t is 0 or 1 to 4; w is 0 or 1 to 4 with the proviso that the sum of t and w is not greater than 5; $R_8$ and $R_9$ are independently selected from hydrogen or an alkyl group having from 1 to 6 carbon atoms; $R_{10}$ is phenyl, phenyl substituted with from 1 to 3 substituents selected from straight or branched alkyl having from 1 to 6 carbon atoms and which is straight or branched, straight or branched alkoxy having from 1 to 6 carbon atoms and which is straight or branched, phenoxy, hydroxy, fluorine, chlorine, bromine, nitro, trifluoromethyl, —COOH, —COOalkyl wherein the alkyl moiety has from 1 to 4 carbon atoms and is straight or branched, or —$(CH_2)_pNR_6R_7$ wherein p is 0 or 1 and each of $R_6$ and $R_7$ is independently selected from hydrogen or an alkyl group having from 1 to 4 carbon atoms, or $R_{10}$ is a 5- or 6-membered monocyclic or fused bicyclic heterocycle containing at least 1 to 4 nitrogen, oxygen or sulfur atoms in at least 1 ring member; or when $R_8$ is hydrogen each of $R_9$ and $R_{10}$ is independently selected from phenyl, phenyl substituted with from 1 to 3 substituents selected from straight or branched alkyl having from 1 to 6 carbon atoms and which is straight or branched, straight or branched alkoxy having from 1 to 6 carbon atoms and which is straight or branched, phenoxy, hydroxy, fluorine, chlorine, bromine, nitro, trifluoromethyl, —COOH, —COOalkyl wherein the alkyl moiety has from 1 to 4 carbon atoms and is straight or branched, or —$(CH_2)_pNR_6R_7$ wherein $R_6$, $R_7$, and p have the meanings defined above, or a 5- or 6-membered monocyclic or fused bicyclic heterocycle containing at least 1 to 4 nitrogen, oxygen, or sulfur atoms in at least 1 ring member;
(c) The group

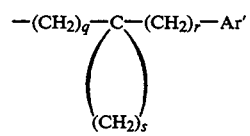

wherein q is 0 or 1 to 3; r is 0, 1, or 2; s is 2 to 6; and Ar' is phenyl,
1- or 2-naphthyl,
phenyl or 1- or 2-naphthyl substituted with alkyl of from 1 to 6 carbon atoms and which is straight or branched,
alkoxy of from 1 to 6 carbon atoms and which is straight or branched,
hydroxy,
benzyloxy, fluorine,
chlorine,
bromine,
nitro,
trifluoromethyl,
—NH—COCH$_3$,
—CONH$_2$,
—COOH,
—COOalkyl wherein alkyl has from 1 to 4 carbon atoms and which is straight or branched,
—CH$_2$COOH,
—CH$_2$CONH$_2$,
—(CH$_2$)$_p$NR$_6$R$_7$ wherein p, R$_6$, and R$_7$ have the meanings defined above;
  (d) a straight or branched hydrocarbon chain having from 1 to 20 carbon atoms and which is saturated or contains from 1 to 3 double bonds;
  (e) an alkyl group having from 1 to 6 carbon atoms wherein the terminal carbon is substituted with hydroxy or —NR$_6$R$_7$ wherein R$_6$ and R$_7$ have the meanings defined hereinabove;
  (f) a 5- or 6-membered monocyclic or fused bicyclic heterocycle containing at least 1 to 4 nitrogen, oxygen or sulfur atoms in at least 1 ring member;
  (g) phenyl or phenyl substituted with from 1 to 3 substituents selected from phenyl,
    alkyl having from 1 to 6 carbon atoms and which is straight or branched,
    alkoxy having from 1 to 6 carbon atoms and which is straight or branched,
    phenoxy,
    hydroxy,
    fluorine,
    chlorine,
    bromine,
    nitro,
    trifluoromethyl,
    —COOH,
    —COOalkyl wherein the alkyl moiety has from 1 to 4 carbon atoms and is straight or branched, or
    —(CH$_2$)$_p$NR$_6$R$_7$ wherein p, R$_6$, and R$_7$ have the meanings defined above;
  (h) 1- or 2-naphthyl which is unsubstituted or substituted with from 1 to 3 substituents selected from phenyl,
    alkyl having from 1 to 6 carbon atoms and which is straight or branched,
    alkoxy having from 1 to 6 carbon atoms and which is straight or branched,
    hydroxy,
    fluorine,
    chlorine,
    bromine,
    nitro,
    trifluoromethyl,
    —COOH,
    —COOalkyl wherein alkyl has from 1 to 4 carbon atoms and which is straight or branched,
    —(CH$_2$)$_p$NR$_6$R$_7$ wherein p, R$_6$, and R$_7$ have the meanings defined above; or
  (i) NR$_1$R$_2$ taken together form a monocyclic heterocyclic group selected from pyrrolidono, piperidino, morpholino, or piperazino, each of which is unsubstituted or is substituted with 1 substituent selected from phenyl, straight or branched alkyl having from 1 to 6 carbon atoms or ω-hydroxyalkyl having from 1 to 6 carbon atoms;
wherein each of R$_3$ and R$_4$ is independently
  (a) hydrogen;
  (b) a straight or branched alkyl group having from 1 to 10 carbon atoms;
  (c) a straight chain alkyl group having from 1 to 10 carbon atoms wherein the terminal carbon atom is substituted with hydroxy or NR$_6$R$_7$ wherein R$_6$ and R$_7$ have the meanings defined above;
wherein R$_5$ is
  (a) hydrogen,
  (b) phenyl which is unsubstituted or is substituted with from 1 to 3 substituents selected from:
    phenyl,
    alkyl having from 1 to 6 carbon atoms and which is straight or branched,
    alkoxy having from 1 to 6 carbon atoms and which is straight or branched,
    phenoxy,
    hydroxy,
    fluorine,
    chlorine,
    bromine,
    nitro,
    trifluoromethyl,
    —COOH,
    —COOalkyl wherein alkyl has from 1 to 4 carbon atoms and which is straight or branched,
    —(CH$_2$)$_p$NR$_6$R$_7$ wherein p, R$_6$, and R$_7$ have the meanings defined above;
  (c) 1- or 2-naphthyl which is unsubstituted or substituted with from 1 to 3 substituents selected from
    phenyl,
    alkyl having from 1 to 6 carbon atoms and which is straight or branched;
    alkoxy having from 1 to 6 carbon atoms and which is straight or branched,
    hydroxy,
    fluorine,
    chlorine,
    bromine,
    nitro,
    trifluoromethyl,
    —COOH,
    —COOalkyl wherein alkyl has from 1 to 4 carbon atoms and is straight or branched,
    —(CH$_2$)$_p$NR$_6$R$_7$ wherein p, R$_6$, and R$_7$ have the meanings defined above;

$$-(CH_2)_t-\underset{R_9}{\overset{R_8}{C}}-(CH_2)_w-R_{10}$$

wherein t is 0 or 1 to 4; w is 0 or 1 to 4 with the proviso that the sum of t and w is not greater than 5; R$_8$ and R$_9$ are independently selected from hydrogen or alkyl having from 1 to 6 carbon atoms, or when R$_8$ is hydrogen, R$_9$ can be the same as R$_{10}$; and R$_{10}$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms and is straight or branched, or —(CH$_2$)$_p$NR$_6$R$_7$ wherein p, R$_6$, and R$_7$ have the meanings defined above;
  (e) the group

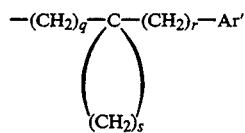

wherein q, r, s, and Ar' have the meanings defined above;

(f) a straight or branched hydrocarbon chain having from 1 to 20 carbon atoms and which is saturated or contains from 1 to 3 double bonds; or (g) a 5- or 6-membered monocyclic or fused bicyclic heterocycle containing at least 1 to 4 nitrogen, oxygen or sulfur atoms in at least 1 ring member; with the provisos that (1) when each $R_1$ and $R_2$ is the group (b) $R_9$ is hydrogen or alkyl having from 1 to 6 carbon atoms, and (2) when 1 of $R_1$ and $R_2$ is the group (c) the other of $R_1$ and $R_2$ is other than (b), (f), or (i); N-oxides thereof, or a pharmaceutically acceptable salt thereof.

U.S. Pat. No. 5,079,137, issued Jan. 7, 1992, to Taguchi, et al., discloses heat-developable color photographic light-sensitive material capable of giving positive color images having high maximum density, low minimum density, and less strain comprising at least a light-sensitive silver halide, a binder, a dye-providing nondiffusible compound capable of releasing a diffusible dye on being reduced, and reducing agent, wherein the light-sensitive material further contains at least one compound represented by the following formula:

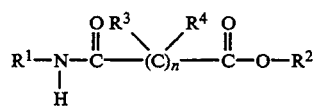

n = 0 or 1 wherein $R^1$ and $R^2$ each represents a substituted or unsubstituted alkyl group, a substituted or unsubstituted aryl group, or a substituted or unsubstituted heterocyclic group, with a proviso that $R^1$ and $R^2$ each represents a group having no redox activity after its cleavage and $R^3$ and $R^4$ each represents a hydrogen atom, a halogen atom, a substituted or unsubstituted alkyl group, a substituted or unsubstituted aryl group, or a substituted or unsubstituted heterocyclic group.

U.S. Pat. No. 5,123,951, issued Jun. 23, 1992, to See, et al., discloses synergistic plant growth regulator compositions containing (i) an ethylene response or ethylene-type response inducing agent and (ii) a malonic acid derivative compound having the formula:

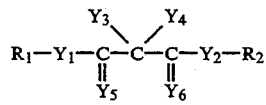

wherein $R_1$, $R_2$, $Y_1$, $Y_3$, $Y_4$, $Y_5$, and $Y_6$ are as defined hereinafter, and in which the amount of compound (ii) used with agent (i) results in a mixture having a greater plant growth regulating effect than the sum total plant growth regulating effect of agent (i) and compound (ii) used alone.

The alpha-aryl or heteroaryl-substituted amide ester ACAT inhibitors of the present invention are not taught by these references. Moreover, the alpha-aryl or heteroaryl-substituted amide ester ACAT inhibitors of the present invention have been found to be characterized as nontoxic in in vivo studies. The nontoxic nature of the compounds of the present invention is particularly advantageous, and will be demonstrated below.

SUMMARY OF THE INVENTION

The present invention provides a class of compounds which have acyl-coenzyme A: cholesterol acyltransferase (ACAT) inhibitory activity and intermediates useful in preparing said compounds of the following general formula:

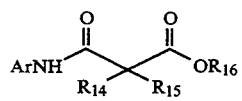

wherein Ar is (a) phenyl substituted with from 2 to 3 substituents selected from phenyl, alkyl having from 1 to 6 carbon atoms and which is straight or branched, alkoxy having from 1 to 6 carbon atoms and which is straight or branched,
phenoxy,
hydroxy,
fluorine,
chlorine,
bromine,
nitro,
trifluoromethyl,
—COOH,
—COOalkyl wherein the alkyl moiety has from 1 to 4 carbon atoms and is straight or branched, or
—$(CH_2)_yNR_{17}R_{18}$ wherein y is 0 or 1 and each of $R_{17}$ and $R_{18}$ is independently selected from hydrogen or an alkyl group having from 1 to 4 carbon atoms;

(b) 1- or 2-naphthyl which is substituted with from 2 to 3 substituents selected from
phenyl,
alkyl having from 1 to 6 carbon atoms and which is straight or branched,
alkoxy having from 1 to 6 carbon atoms and which is straight or branched,
hydroxy,
fluorine,
chlorine,
bromine,
nitro,
trifluoromethyl,
—COOH,
—COOalkyl wherein alkyl has from 1 to 4 carbon atoms and which is straight or branched,
—$(CH_2)yNR17R18$ wherein y, R17, and R18 have the meanings defined above; or;

(c)

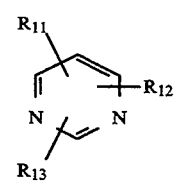

wherein $R_{11}$, $R_{12}$, and $R_{13}$ are each independently
(a) hydrogen, (b) alkyl of from 1 to 4 carbon atoms and which is straight or branched;
(c) alkoxy of from 1 to 3 carbon atoms and which is straight or branched;
(d) alkylthio of from 1 to 3 carbon atoms and which is straight or branched;
(e) fluorine;
(f) chlorine;
(g) bromine;

wherein $R_{14}$ and $R_{15}$ are each independently
(a) phenyl, phenyl substituted with from 1 to 3 substituents selected from straight or branched chain alkyl having from 1 to 4 carbon atoms, straight or branched alkoxy having from 1 to 4 carbon atoms, straight or branched alkylthio having from 1 to 4 carbon atoms, F, Cl, Br, $CF_3$, CN, $NO_2$, phenyl, cycloalkyl of from 3 to 8 carbon atoms;
(b) 1- or 2-naphthyl which is unsubstituted or substituted with from 1 to 3 substituents selected from straight or branched alkyl having from 1 to 4 carbon atoms, straight or branched alkoxy having from 1 to 3 carbon atoms;
(c) hydrogen;
(d) fluorine;
(e) straight or branched chain alkyl having from 1 to 4 carbon atoms;
(f) a 5- or 6-membered monocyclic or fused bicyclic heterocycle containing at least 1 to 4 nitrogen, oxygen, or sulfur atoms in at least 1 ring member;
(g) hydroxy; and
(h) —$(CH_2)_yNR'R''$ wherein y has the same meaning as above and each of R' and R'' is independently selected from hydrogen, straight or branched alkyl of from 1 to 6 carbon atoms optionally substituted with hydroxyl, cycloalkyl of from 5 to 8 carbon atoms, or where R' and R'' taken together also represent

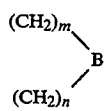

wherein m and n are each an integer of from 2 to 3 and B is a direct bond, or oxygen, sulfur; with the proviso that $R_{14}$ and $R_{15}$ are not both hydrogen, fluorine, or a straight or branched chain alkyl or a combination thereof;

wherein $R_{16}$ is
(a) hydrogen,
(b) phenyl which is unsubstituted or is substituted with from 1 to 3 substituents selected from:
phenyl,
alkyl having from 1 to 6 carbon atoms and which is straight or branched,
alkoxy having from 1 to 6 carbon atoms and which is straight or branched,
phenoxy,
hydroxy,
fluorine,
chlorine,
bromine,
nitro,
trifluoromethyl,
—COOH,
—COOalkyl wherein alkyl has from 1 to 4 carbon atoms and which is straight or branched, —$(CH_2)_yNR_{17}R_{18}$ wherein y, $R_{17}$, and $R_{18}$ have the meanings defined above;
(c) 1- or 2-naphthyl which is unsubstituted or substituted with from 1 to 3 substituents selected from
phenyl,
alkyl having from 1 to 6 carbon atoms and which is straight or branched;
alkoxy having from 1 to 6 carbon atoms and which is straight or branched,
hydroxy,
fluorine,
chlorine,
bromine,
nitro,
trifluoromethyl,
—COOH,
—COOalkyl wherein alkyl has from 1 to 4 carbon atoms and is straight or branched,
—$(CH_2)_yNR_{17}R_{18}$ wherein y, $R_{17}$, and $R_{18}$ have the meanings defined above;
(d) the group

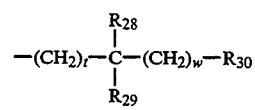

wherein t is 0 or 1 to 4; w is 0 or 1 to 4 with the proviso that the sum of t and w is not greater than 5; $R_{28}$ and $R_{29}$ are independently selected from hydrogen or alkyl having from 1 to 6 carbon atoms, or when $R_{28}$ is hydrogen, $R_{29}$ can be the same as $R_{30}$; and $R_{30}$ is phenyl or phenyl substituted with from 1 to 3 substituents selected from straight or branched alkyl having from 1 to 6 carbon atoms, straight or branched alkoxy having from 1 to 6 carbon atoms, phenoxy, hydroxy, fluorine, chlorine, bromine, nitro, trifluoromethyl, —COOH, COOalkyl wherein alkyl has from 1 to 4 carbon atoms and is straight or branched, or —$(CH_2)_yNR_{17}R_{18}$ wherein y, $R_{17}$, and $R_{18}$ have the meanings defined above;
(e) the group

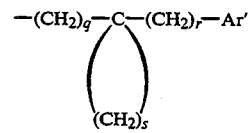

wherein q is 0 or 1 to 3; r is 0, 1, or 2; s is 2 to 6; and $Ar^1$ is
phenyl,
1- or 2-naphthyl,
phenyl or 1- or 2-naphthyl substituted with alkyl of from 1 to 6 carbon atoms and which is straight or branched,
alkoxy of from 1 to 6 carbon atoms and which is straight or branched,
hydroxy,
benzyloxy,
fluorine,
chlorine,
bromine,
nitro,
trifluoromethyl,
—NH—$COCH_3$,
—$CONH_2$,
—COOH, —COOalkyl wherein alkyl has from 1 to 4 carbon atoms and which is straight or branched,
—$CH_2COOH$,
—$CH_2CONH_2$,
—$(CH_2)_yNR_{17}R_{18}$ wherein y, $R_{17}$, and $R_{18}$ have the meanings defined above;

(f) a straight or branched hydrocarbon chain having from 1 to 20 carbon atoms and which is saturated or contains from 1 to 3 double bonds; or (g) a 5- or 6-membered monocyclic or fused bicyclic heterocycle containing at least 1 to 4 nitrogen, oxygen or sulfur atoms in at least 1 ring member;

N-oxides thereof, or a pharmaceutically acceptable salt thereof.

This invention also provides pharmaceutical compositions containing the compounds of Formula I and methods of treating hypercholesterolemia and atherosclerosis using the compounds of Formula I.

DETAILED DESCRIPTION OF INVENTION

The compounds of the present invention provide a novel class of amide esters which are ACAT inhibitors rendering them useful in treating hypercholesterolemia and atherosclerosis.

Illustrative examples of straight or branched alkyl groups having from 1 to 4 or 1 to 6 carbon atoms includes methyl, ethyl, n-propyl, isopropyl, n-butyl, pentyl, and hexyl.

Illustrative examples of straight or branched saturated hydrocarbon groups having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-ethyltetradecyl, and n-octadecyl groups.

Illustrative straight or branched hydrocarbon groups having from 1 to 20 carbon atoms and having from 1 to 3 double bonds are ethenyl, 2-propenyl, 2-butenyl, 3-pentenyl, 2-octenyl, 5-nonenyl, 4-undecenyl, 5-hepadecenyl, 3-octadecenyl, 9-octadecenyl, 2,2-dimethyl-11-eicosenyl, 9, 12-octadecadienyl, and hexadecenyl.

Straight or branched alkoxy groups having from 1 to 6 carbon atoms include, for example, methoxy, ethoxy, n-propoxy, t-butoxy, and pentyloxy.

A 5- or 6-membered monocyclic or fused bicyclic heterocycle is a monocyclic or fused bicyclic aromatic ring containing at least 1 to 4 hetero atoms in at least 1 ring, such as nitrogen, oxygen or sulfur or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, oxazolyl, isoxazolyl, triazolyl, tetrazolyl, imidazolyl, benzothiazolyl, indolyl, quinolinyl, isoquinolinyl, or N-oxides of a heterocycle containing a nitrogen atom.

More specifically, such heterocycle may be 2- or 3-thienyl; 2- or 3-furanyl; 2-, or 3-, or 4-pyridyl or -pyridyl-N-oxides; 2, 4, or 5-pyrimidinyl; 3- or 4-pyridazinyl; 2-pyrazinyl; 2-or 3-pyrrolyl; 3-, 4-, or 5-pyrazolyl, 3-, 4-, or 5-isoxazolyl; 3-, 4-, or 5-oxazolyl; 3-, 4-, or 5-isothiazolyl; 5-tetrazolyl; 3- or 5-(1,2,4-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzolthiazolyl; or 2-, 3-, 4-, 5-, 6-, or 7-benzothienyl.

Preferred compounds of this invention are those wherein $R_{14}$ and $R_{15}$ are selected from pyridine, phenyl, or substituted phenyl. It is particularly preferred wherein one of $R_{14}$ and $R_{15}$ is hydrogen and the other is selected from pyridine, phenyl, or substituted phenyl. More preferred is where one of $R_{14}$ and $R_{15}$ is hydrogen and the other is phenyl.

Preferred compounds of this invention are also those wherein Ar is a di- or trisubstituted phenyl. More preferred is where Ar is 2,6-disubstituted or 2,4,6-trisubstituted phenyl. Most preferred is where Ar is 2,6-bis(1-methylethyl)phenyl or 2,4,6-trimethoxyphenyl.

Preferred compounds of this invention are also those wherein $R_{16}$ is a straight or branched hydrocarbon chain having 10 to 20 carbon atoms. More preferred is where $R_{16}$ is dodecyl, tridecyl, 1,1-dimethyltridecyl, 1-methyltridecyl, or 1-methylundecyl.

Pharmaceutically acceptable salts of the compounds of Formula I are also included as a part of the present invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of the salt with a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The class of acids suitable for the formation of nontoxic, pharmaceutically acceptable salts is well known to practitioners of the pharmaceutical formulation arts. (See, for example, Stephen N. Berge, et al. *J Pharm Sciences*, 66:1–19 (1977)).

The compounds of the present invention may also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired by methods known in the art as, for example, the separation of stereoisomers in chiral chromatographic columns.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

As shown by the data presented below in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field FJ and Salone RG, *Biochemica et..Biophysica* 712:557–570 (1982). The test assesses the ability of a test compound to inhibit the acylation of cholesterol by oleic acid by measuring the amount of radio labeled cholesterol oleate formed from radiolabeled oleic acid in a tissue preparation containing rabbit intestinal microsomes.

The data appear in Table I where they are expressed as IC50 values; i.e., the concentration of test compound required to inhibit the activity of the enzyme by 50%.

TABLE I

| Example | LAI IC$_{50}$ ($\mu$M) |
|---|---|
| 1 | 0.022 |
| 2 | >5 |
| 3 | 0.010 |
| 4 | 0.013 |
| 5 | 0.016 |
| 6 | 0.013 |
| 7 | 0.040 |
| 8 | 0.050 |
| 9 | >1.0 |
| 10 | 0.013 |
| 11 | 0.012 |
| 12 | 0.012 |
| 13 | 0.037 |
| 14 | 0.200 |
| 15 | 0.011 |
| 16 | 0.072 |
| 17 | 0.030 |
| 18 | 0.013 |
| 19 | 0.008 |

The compounds were also evaluated in an in vivo screen designated APCC whereby male Sprague-Dawley rats (200 to 225 g) were randomly divided into treatment groups and dosed at 4 PM with either vehicle (CMC/Tween) or suspensions of compounds in vehicle. The normal chow diet was then replaced with the PCC diet with either 1% or 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher-s least significant test.

The data appear in Table II where they are expressed as % change.

TABLE II

| Example | APCC % Change TC |
|---|---|
| 1 | −61 |
| 2 | — |
| 3 | −63 |
| 4 | −37 |
| 5 | −49 |
| 6 | −58 |
| 7 | −67 |
| 8 | −71 |
| 9 | −20 |
| 10 | −56 |
| 11 | −67 |
| 12 | −26 |
| 13 | −26 |
| 14 | −25 |
| 15 | −72 |
| 16 | −37 |
| 17 | −59 |
| 18 | −51 |
| 19 | −43 |

As indicated above, and shown by the data presented below, the compounds of the present invention have been found to be characterized as nontoxic in in vivo studies. The nontoxic nature of the compounds of the present invention is particularly advantageous and surprising in light of toxicity screens of previously disclosed amide ester ACAT inhibitors, but which are not substituted aryl or heteroaryl at the alpha-position. The compounds of the present invention are thus useful in pharmaceutical formulations for the treatment of hypercholesterolemia or atherosclerosis.

The nontoxic nature of representative compounds of the present invention was measured and compared against alpha-unsubstituted amide ester ACAT inhibitors using an in vivo toxicity screen developed by Dominick, et al., *Toxicologic Pathology*, Vol. 21, No. 1, p. 54–62, 1993.

Male guinea pigs of the Hartley strain (450–500 g) were obtained from Charles River and randomly divided into treatment groups. They were fed standard guinea pig chow ad libitum and dosed daily (AM) by gavage (100 mg/kg). The test compounds were dissolved or suspended in an oleic acid vehicle to facilitate absorption. After 2 weeks the animals were sacrificed by $CO_2$ asphyxiation in the nonfasted state 16 hours after the last dose. Adrenal glands were weighed, fixed in 10% formalin, processed by routine paraffin techniques, sectioned, and then stained with hematoxylin and eosin for light microscopy. Toxicity was defined by the incidence, severity, and complexity of adrenal histopathologic alterations in the zona fasciculata (e.g., adrenal cortical atrophy, increased coarse vacuolation, single-cell necrosis, inflammatory cell infiltrates, mineralization/ectopic bone formation, and increased cytoplasmic eosinophilia).

The results indicated that the alpha-unsubstituted amide ester compound, (±)3-[[2,6-bis(1-methylethyl)-phenyl]amino]-3-oxo-propanoic acid, 1-methyltridecyl ester, is classed as highly toxic to the adrenal gland. Cytotoxic zonal atrophy of the zona fasciculata (near complete loss of zona fasciculata due to cortical cell necrosis and degeneration) in six of six treated animals and atrophy of the zona reticularis in two of six animals. Necrosis of the adrenal cortex was observed in four of six animals and inflammatory cell infiltrates were present in four of six animals. Increased coarse vacuoles were present in two of six animals.

The results further indicated that the alpha-aryl or heteroaryl-substituted amide ester compounds, of the present invention, benzeneacetic acid, (±)-[[[2,6-bis(1-methylethyl)phenyl]amino]carbonyl]-1-methyltridecyl ester and benzene acetic acid, (±)-[[[2,6-bis(1-methylethyl)phenyl]amino]carbonyl]dodecyl ester, respectively, are classed as nontoxic to the adrenal gland having increased coarse vacuoles in only one of six animals and classed as nontoxic to the adrenal gland having increased coarse vacuoles in five of six animals.

In therapeutic use as agents for treating hypercholesterolemia or atherosclerosis, the compounds of Formula I are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of general Formula I are prepared as shown in Charts I and II hereof wherein the various substituent groups Ar, $R_{14}$, $R_{15}$, and $R_{16}$ have the meanings defined in Formula I. In Chart I, to a THF solution of LDA at $-40°$ C. was added ester (1). After anion formation, the solution was cooled to $-78°$ C. and treated with an aryl isocyanate. Quenching with 1N HCl gives ester (2). This is treated with methanolic NaOH at room temperature to give acid (3). This acid is then coupled with an alcohol ($R_{16}OH$) using dicyclohexylcarbodiimide (DCC) in dichloromethane at $-10°$ C. to $0°$ C. to yield compounds of structural type (4).

The compounds of this invention may also be prepared as set forth in Chart II hereof. To a substituted acetic acid derivative (5) was coupled alcohol ($R_{16}OH$) using DCC in dichloromethane at $-10°$ C. to give ester (6). This was then treated with LDA at $-78°$ C. in THF, followed by the addition of an aryl isocyanate to give compounds of structural type (4).

The following specific examples further illustrate the invention.

EXAMPLE 1

(±)-Benzeneacetic acid, α-[[[2,6-bis(1-methylethyl)phenyl]amino]carbonyl]-, 1-methyltridecyl ester (a) (±)-Benzeneacetic acid, α-[[[2,6-bis(1-methylethyl)phenyl]amino]carbonyl]ethyl ester, Example 2

To a THF solution (40 mL) of diisopropylamine (22.53 mL, 0.16 tool) at $-40°$ C. under $N_2$ with stirring was added n-BuLi (100.5 Ml, 1.6M, 0.1607 mol). After 10 minutes a solution of ethyl phenyl acetate (24 g, 0.146 tool) in THF (150 mL) was added. A yellow suspension resulted, this was then stirred at $-78°$ C. for 30 minutes before a THF (80 mL) solution of 2,6-diisopropylphenylisocyanate (31.24 g, 0.146 mol) was added dropwise. The resulting solution was stirred at $-78°$ C. for 3 hours before quenching with 1N HCl (120 mL). Ethyl acetate (300 mL) was added and the organic layer separated. This was washed with water (2×200 mL), brine (1×200 mL), and dried over anhydrous magnesium sulphate. Filtration, followed by concentration in vacuo, gave a white solid which was recrystallized from ethyl acetate/hexane to give 42.25 g of the title compound, mp 175°–177° C.

(b) (±)-Benzeneacetic acid, α-[[[2,6-bis(1-methylethyl)phenyl]amino]carbonyl]

To a methanol (750 mL)/THF (100 mL) solution of the compound (33.55 g, 0.0913 tool) obtained above in step (a) was added 1N aqueous NaOH (91.3 mL, 0.0913 mol). The resulting solution was stirred overnight at room temperature. This was then concentrated in vacuo and the resulting residue was redissolved in water (500 mL). This was washed with ethyl ether (2×200 mL) and the aqueous solution acidified with 1N HCl. A white solid precipitated. This was filtered and air dried overnight to yield the title compound, mp 201°–203° C.

(c) To a dichloromethane (500 mL) solution of the compound (25 g, 0.0736 mol) obtained above was added 2-tetradecanol (15.79 g, 0.0736 mol) at $0°$ C. under $N_2$ with stirring. To this was added dicyclohexylcarbodiimide (16.71 g, 0.081 mol). An immediate precipitate resulted. This was allowed to warm to room temperature overnight. This solution was then filtered. After concentration in vacuo, flash chromatography (eluting with 10% to 25% ethyl acetate/hexane) gave 31.72 g of the title compound, Example 1, mp 94°–97° C.

When in the general procedure of Example 1 only using an appropriate amount of the alcohol listed below in place of 2-tetradecanol, the products listed below in Table 2 were obtained.

TABLE 2

| Example | Alcohol | Product |
|---|---|---|
| 3 | 1-dodecanol | (±)-Benzeneacetic acid, α-[[[2,6-bis(1-methylethyl)phenyl]amino]carbonyl]-, dodecyl ester, mp 102–104° C. |
| 4 | 2-dodecanol | (±)-Benzeneacetic acid, α-[[[2,6-bis(1-methylethyl)phenyl]amino]carbonyl]-, 1-methylundecyl ester, mp 95–97° C. |
| 5 | 1-tetradecanol | (±)-Benzeneacetic acid, α-[[[2,6-bis(1-methylethyl)phenyl]amino]carbonyl]-, tetradecyl ester, mp 99–101° C. |
| 6 | 1-decanol | (±)-Benzeneacetic acid, α-[[[2,6-bis(1-methylethyl)phenyl]amino]carbonyl]-, decyl ester, mp 104–105° C. |
| 7 | 2-heptanol | (±)-Benzeneacetic acid, α-[[[2,6-bis(1-methylethyl)- |

TABLE 2-continued

| Example | Alcohol | Product |
|---|---|---|
| | | phenyl]amino]carbonyl]-, 1-methylhexyl ester, mp 108–110° C. |
| 8 | 1-heptanol | (±)-Benzeneacetic acid, α-[[[2,6-bis(1-methylethyl)-phenyl]amino]carbonyl]-, heptyl ester, mp 134–135° C. |
| 9 | 1-propanol | (±)-Benzeneacetic acid, α-[[[2,6-bis(1-methylethyl)-phenyl]amino]carbonyl]-, propyl ester, mp 148–150° C. |
| 10 | 1-octanol | (±)-Benzeneacetic acid, α-[[[2,6-bis(1-methylethyl)-phenyl]amino]carbonyl]-, octyl ester, mp 120–122° C. |
| 11 | 1-nonanol | (±)-Benzeneacetic acid, α-[[[2,6-bis(1-methylethyl)-phenyl]amino]carbonyl]-, nonyl ester, mp 124–126° C. |
| 12 | 2-methyl-2-tetradecanol | (±)-Benzeneacetic acid, α-[[[2,6-bis(1-methylethyl)-phenyl]amino]carbonyl]-, 1,1-dimethyltridecyl ester, mp 89–91° C. |
| 13 | 1-hexadecanol | (±)-Benzeneacetic acid, α-[[[2,6-bis(1-methylethyl)-phenyl]amino]carbonyl]-, hexadecyl ester, mp 78–81° C. |
| 14 | 1-octadecanol | (±)-Benzeneacetic acid, α-[[[2,6-bis(1-methylethyl)-phenyl]amino]carbonyl]-, octadecyl ester, mp 79–82° C. |
| 15 | 2-methyl-2-hexanol | (±)-Benzeneacetic acid, α-[[[2,6-bis(1-methylethyl)-phenyl]amino]carbonyl]-, 1,1-dimethylpentyl ester, mp 98–101° C. |
| 16 | 2-hexadecanol | (±)-Benzeneacetic acid, α-[[[2,6-bis(1-methylethyl)-phenyl]amino]carbonyl]-, 1-methylpentadecyl ester, mp 89–90° C. |

When in the general procedure of Example 1, only using an appropriate amount of (±)-Benzeneacetic acid, α-[[(2,4,6-trimethoxyphenyl)amino]carbonyl]-, instead of (±)-Benzeneacetic acid, α-[[[2,6-bis(1-methylethyl)-phenyl]amino]carbonyl]-, Example 17 is obtained.

EXAMPLE 17

(±)-Benzeneacetic acid, α-[[(2,4,6-trimethoxyphenyl)amino]carbonyl]-, 1-methyltridecyl ester, mp 84°–86° C.

EXAMPLE 18

(±) -Benzeneacetic acid, α-[[(2,4,6-trimethoxyphenyl)amino]carbonyl]-, dodecyl ester (a) Benzeneacetic acid, dodecyl ester. To a dichloromethane (100 mL) solution of phenylacetic acid (5 g, 0.0367 mol) at 0° C. under N₂ with stirring was added 1-dodecanol (0.0367 mol, 6.84 g). This solution was allowed to warm to room temperature overnight. The solution was then filtered and concentrated in vacuo. Flash chromatography (eluting with 10% EtOAc-Hex) gave 6.4 g of the title compound. $^1$H NMR (CDCl₃): δ 7.2–7.4 (m, 5H); 4.1 (tr, 2H); 3.6 (s, 2H); 1.6 (m, 2H); 1.3 (s, 18H), 0.9 (tr, 3H) ppm.

(b) To a THF solution (30 mL) of diisopropylamine (1.52 mL, 0.0108 mol) at −40° C. under N₂ with stirring was added n-BuLi (5.16 mL, 2.1M, 0.0108 mol). After 10 minutes a THF solution (20 mL) of the compound obtained in Step (a) (3 g, 0.00985 mol) was added. This was then stirred at −78° C. for 1 hour and then a THF solution (15 mL) of 2,4,6-trimethoxyphenylisocyanate (2.06 g, 0. 00985 mol) was added dropwise. After stirring for an additional 1 hour at −78° C., the reaction was quenched by the addition of 1N HCl (10 mL). The solution was warmed to room temperature and the organic layer was separated. This was washed with water (1×100 mL), brine (1×100 mL), and dried over MgSO₄. Flash chromatography (eluting with 25% EtOAc-Hex) gave 1.1 g of the title compound, mp 93°–95° C.

When in the general procedure of Example 18, 2-pyridineacetic acid, dodecyl ester is used instead of benzeneacetic acid, dodecyl ester and 2,6-diisopropyl-phenylisocyanate is used instead of 2,4,6-trimethoxyphenylisocyanate, Example 19 is obtained.

EXAMPLE 19

(±)-2-pyridineacetic acid, α-[[[2,6-bis(1-methylethyl)phenyl]amino]carbonyl]-, dodecyl ester, mp 44°–47° C.

EXAMPLE 20

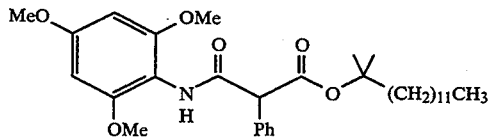

(±)-Benzeneacetic acid, α-[[(2,4,6-trimethoxyphenyl)amino]carbonyl]-1,1-dimethyltridecyl ester

EXAMPLE 21

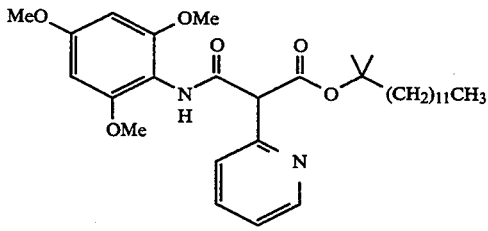

(±)-2-pyridineacetic acid, α-[[(2,4,6-trimethoxyphenyl)amino]carbonyl]-, 1,1-dimethyltridecyl ester

EXAMPLE 22

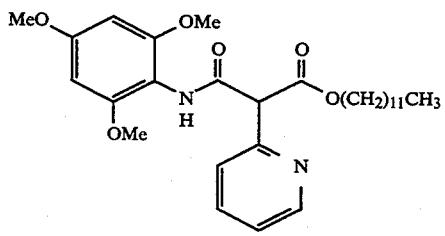

(±)-2-pyridineacetic acid,
α-[[(2,4,6-trimethoxyphenyl)amino]carbonyl]-, dodecyl ester

EXAMPLE 23

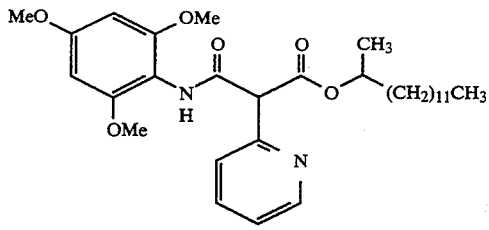

(±)-2-pyridineacetic acid,
α-[[(2,4,6-trimethoxyphenyl)amino]carbonyl]-,
1-methyl tridecyl ester

EXAMPLE 24

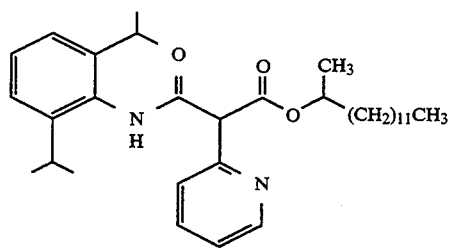

(±)-2-pyridineacetic acid,
α-[[[2,6-bis(1-methylethyl)phenyl]amino]carbonyl]-,
1-methyltridecyl ester

EXAMPLE 25

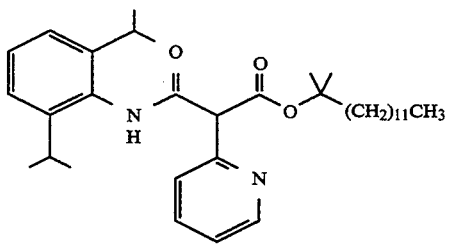

(±)-2-pyridineacetic acid,
α-[[[2,6-bis(1-methyethyl)phenyl]amino]carbonyl]-,
1,1-dimethyltridecyl ester

EXAMPLE 26

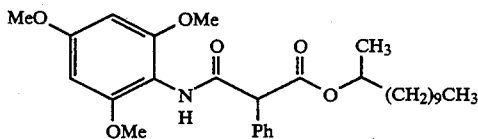

(±)-Benzeneacetic acid,
α-[[(2,4,6-trimethoxyphenyl)amino]carbonyl]-,
1-methylundecyl ester

EXAMPLE 27

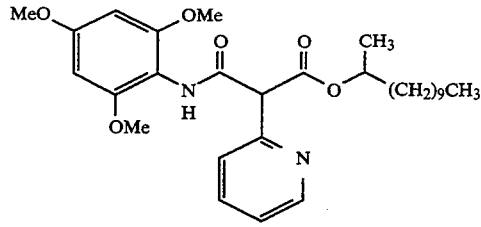

(±)-2-pyridineacetic acid,
α-[[(2,4,6-trimethoxyphenyl)amino]carbonyl]-,
1-methylundecyl ester

EXAMPLE 28

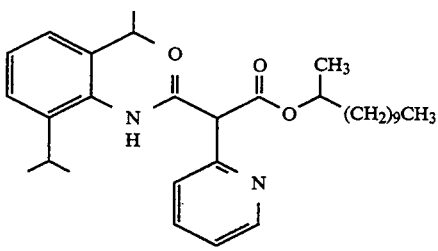

(+)-2-pyridineacetic acid,
α-[[[2,6-bis(1-methylethyl)phenyl]amino]carbonyl]-,
1-methylundecyl ester

CHART I

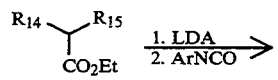

(1)

(2)

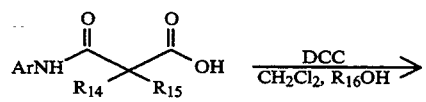

(3)

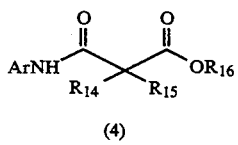

(4)

CHART II

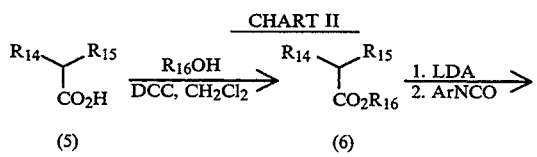
(5) → (6)

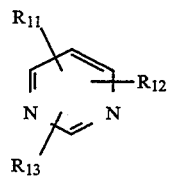
(c)

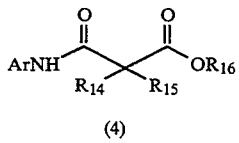
(4)

We claim:
1. A compound having the formula

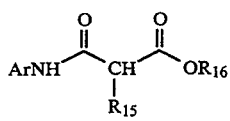
I wherein Ar is
(a) phenyl substituted with from 2 to 3 substituents selected from phenyl,
alkyl having from 1 to 6 carbon atoms and which is straight or branched,
alkoxy having from 1 to 6 carbon atoms and which is straight or branched,
phenoxy,
hydroxy,
fluorine,
chlorine,
bromine,
nitro,
trifluoromethyl,
—COOH,
—COOalkyl wherein the alkyl moiety has from 1 to 4 carbon atoms and is straight or branched, or
—$(CH_2)_y NR_{17}R_{18}$ wherein y is 0 or 1 and each of $R_{17}$ and $R_{18}$ is independently selected from hydrogen or an alkyl group having from 1 to 4 carbon atoms;
(b) 1- or 2-naphthyl which is substituted with from 2 to 3 substituents selected from
phenyl,
alkyl having from 1 to 6 carbon atoms and which is straight or branched,
alkoxy having from 1 to 6 carbon atoms and which is straight or branched,
hydroxy,
fluorine,
chlorine,
bromine,
nitro,
trifluoromethyl,
—COOH,
—COOalkyl wherein alkyl has from 1 to 4 carbon atoms and which is straight or branched,
—$(CH_2)_y NR_{17}R_{18}$ wherein y, $R_{17}$, and $R_{18}$ have the meanings defined above; or;
(c)

wherein $R_{11}$, $R_{12}$, and $R_{13}$ are each independently
(a) hydrogen,
(b) alkyl of from 1 to 4 carbon atoms and which is straight or branched;
(c) alkoxy of from 1 to 3 carbon atoms and which is straight or branched;
(d) alkylthio of from 1 to 3 carbon atoms and which is straight or branched;
(e) fluorine;
(f) chlorine;
(g) bromine;
wherein $R_{15}$ is
phenyl, phenyl substituted with from 1 to 3 substituents selected from straight or branched chain alkyl having from 1 to 4 carbon atoms, straight or branched alkoxy having from 1 to 4 carbon atoms, straight or branched alkylthio having from 1 to 4 carbon atoms, F, Cl, Br, $CF_3$, CN, $NO_2$, phenyl, cycloalkyl of from 3 to 8 carbon atoms;
wherein $R_{16}$ is
a straight or branched hydrocarbon chain having from 10 to 20 carbon atoms and which is saturated or contains from 1 to 3 double bonds;
N-oxides thereof, or a pharmaceutically acceptable salt thereof.

2. A compound of claim 1 wherein Ar is 2,6-disubstituted or 2,4,6-trisubstituted phenyl.
3. A compound of claim 1 wherein Ar is 2,6-bis(1-methylethyl)phenyl or 2,4,6-trimethoxyphenyl.
4. A compound of claim 1 wherein $R_{15}$ is phenyl.
5. A compound of claim 1 wherein $R_{15}$ is substituted phenyl.
6. A compound of claim 1 wherein Ar is 2,6-disubstituted or 2,4,6-trisubstituted phenyl and $R_{15}$ is phenyl.
7. A compound of claim 1 wherein Ar is 2,6-disubstituted or 2,4,6-trisubstituted phenyl and $R_{15}$ is substituted phenyl.
8. A compound of claim 6 which is:
(±)-Benzeneacetic acid, α-[[[2,6-bis(1-methylethyl)phenyl]amino]carbonyl]-, 1-methyl tridecyl ester;
(±)-Benzeneacetic acid, α-[[[2,6-bis(1-methylethyl)phenyl]amino]carbonyl]-, dodecyl ester;
(±)-Benzeneacetic acid, α-[[[2,6-bis(1-methylethyl)phenyl]amino]carbonyl]-, 1-methylundecyl ester;
(±)-Benzeneacetic acid, α-[[[2,6-bis(1-methylethyl)phenyl]amino]carbonyl]-, tetradecyl ester;
(±)-Benzeneacetic acid, α-[[[2,6-bis(1-methylethyl)phenyl]amino]carbonyl]-, decyl ester;
(±)-Benzeneacetic acid, α-[[[2,6-bis(1-methylethyl)phenyl]amino]carbonyl]-, 1,1-dimethyltridecyl ester;
(±)-Benzeneacetic acid, α-[[[2,6-bis(1-methylethyl)phenyl]amino]carbonyl]-, hexadecyl ester;
(±)-Benzeneacetic acid, α-[[[2,6-bis(1-methylethyl)phenyl]amino]carbonyl]-, octadecyl ester;
(±)-Benzeneacetic acid, α-[[[2,6-bis(1-methylethyl)phenyl]amino]carbonyl]-, 1-methylpentadecyl ester;

(±)-Benzeneacetic acid, α-[[(2,4,6-trimethoxyphenyl)amino]carbonyl]-, 1-methyltridecyl ester;

(±)-Benzeneacetic acid, α-[[(2,4,6-trimethoxyphenyl)amino]carbonyl]-, dodecyl ester;

(±)-Benzeneacetic acid, α-[[(2,4,6-trimethoxyphenyl)amino]carbonyl]-1,1-dimethyltridecyl ester; or (±)-Benzeneacetic acid, α-[[2,4,6-trimethoxyphenyl)amino]carbonyl]-, 1-methylundecyl ester.

9. A pharmaceutical composition comprising a compound of claim 1, N-oxides thereof, or a pharmaceutically acceptable salt thereof, and a pharmaceutically acceptable carrier.

10. A pharmaceutical composition comprising a compound of claim 1 wherein Ar is disubstituted or trisubstituted phenyl and a pharmaceutically acceptable carrier.

11. A pharmaceutical composition comprising a compound of claim 8 and a pharmaceutically acceptable carrier.

12. A method of treating atherosclerosis in a patient in need of treatment which comprises administering to said patient an effective amount of a compound of claim 1.

13. A method of treating atherosclerosis in a patient in need of treatment which comprises administering to said patient an effective amount of a compound of claim 11.

* * * * *